(12) United States Patent
Hansson et al.

(10) Patent No.: US 11,234,828 B2
(45) Date of Patent: Feb. 1, 2022

(54) PROSTHESIS FOR RECONSTRUCTION OF DISTAL AND PROXIMAL RADIOULNAR JOINTS

(71) Applicant: SWEMAC INNOVATION AB, Linköping (SE)

(72) Inventors: Henrik Hansson, Vreta Kloster (SE); Lars Oster, Lidköping (SE); Michael Ullman, Onsala (SE); Lars Adolfsson, Linköping (SE)

(73) Assignee: SWEMAC INNOVATION AB, Linkoping (SE)

( * ) Notice: Subject to any disclaimer, the term of this patent is extended or adjusted under 35 U.S.C. 154(b) by 95 days.

(21) Appl. No.: 16/342,568

(22) PCT Filed: Oct. 28, 2016

(86) PCT No.: PCT/EP2016/076075
§ 371 (c)(1),
(2) Date: Apr. 17, 2019

(87) PCT Pub. No.: WO2018/077421
PCT Pub. Date: May 3, 2018

(65) Prior Publication Data
US 2019/0254833 A1   Aug. 22, 2019

(51) Int. Cl.
*A61F 2/38* (2006.01)
*A61F 2/42* (2006.01)
(Continued)

(52) U.S. Cl.
CPC .......... *A61F 2/4261* (2013.01); *A61B 17/151* (2013.01); *A61F 2002/305* (2013.01);
(Continued)

(58) Field of Classification Search
CPC .................. A61F 2/4261; A61F 2/3804; A61F 2002/3809; A61F 2002/3813;
(Continued)

(56) References Cited

U.S. PATENT DOCUMENTS

| | | | |
|---|---|---|---|
| 5,108,444 A | | 4/1992 | Branemark |
| 5,938,699 A | * | 8/1999 | Campbell ............. A61F 2/4261 623/21.13 |

(Continued)

FOREIGN PATENT DOCUMENTS

| | | |
|---|---|---|
| DE | 29911714 | 6/2000 |
| EP | 1191908 | 6/2004 |

(Continued)

*Primary Examiner* — Christopher D. Prone
(74) *Attorney, Agent, or Firm* — Tarolli, Sundheim, Covell & Tummnio LLP

(57) ABSTRACT

A prosthesis for reconstruction of a distal radioulnar joint, after resection of a part of the ulna, includes a first prosthesis member, fixation members and a second prosthesis member. The first prosthesis member is configured for fixation to the distal end portion of the ulna. The fixation members are configured to extend into the radius via said distal end portion of the ulna for locking said distal end portion of the ulna to the radius. The second prosthesis member is configured for fixation to the ulna close to said distal end portion of the ulna. The second prosthesis member is also configured to extend into said space for being joined with the first prosthesis member in a manner which allows said first and second prosthesis members to at least pivot and rotate relative to each other.

21 Claims, 13 Drawing Sheets

(51) Int. Cl.
*A61B 17/15* (2006.01)
*A61F 2/30* (2006.01)

(52) U.S. Cl.
CPC ............ *A61F 2002/3085* (2013.01); *A61F 2002/30205* (2013.01); *A61F 2002/30242* (2013.01); *A61F 2002/30331* (2013.01); *A61F 2002/30405* (2013.01); *A61F 2002/30469* (2013.01); *A61F 2002/30649* (2013.01); *A61F 2002/30878* (2013.01); *A61F 2002/4269* (2013.01)

(58) Field of Classification Search
CPC ...... A61F 2002/4264; A61F 2002/4266; A61F 2002/4269; A61F 2002/2896; A61F 2002/3827; A61F 2002/3831
See application file for complete search history.

(56) References Cited

U.S. PATENT DOCUMENTS

| | | |
|---|---|---|
| 8,388,689 B2 | 3/2013 | Orbay et al. |
| 2006/0282169 A1 | 12/2006 | Felt et al. |
| 2015/0305788 A1 | 10/2015 | Hansson et al. |

FOREIGN PATENT DOCUMENTS

| | | |
|---|---|---|
| FR | 2660856 | 10/1991 |
| WO | 0101892 | 1/2001 |
| WO | 2009136852 | 11/2009 |

\* cited by examiner

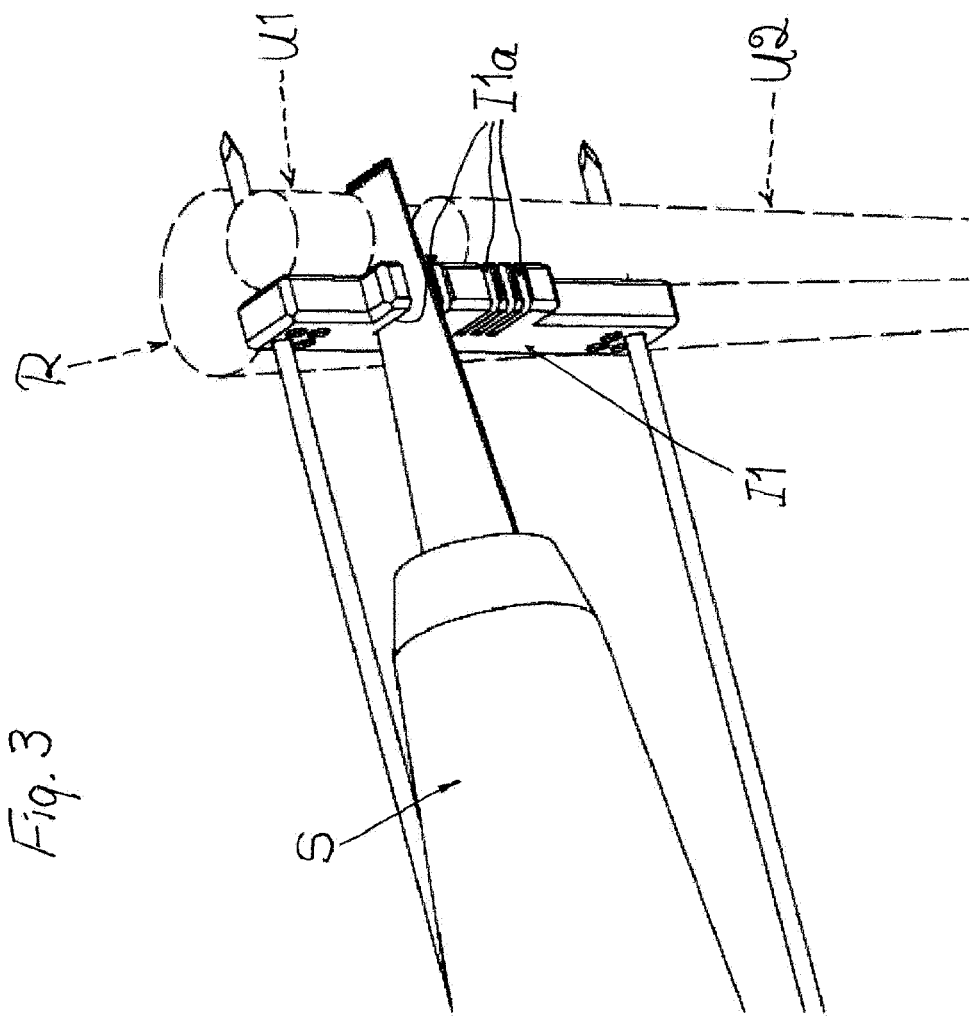

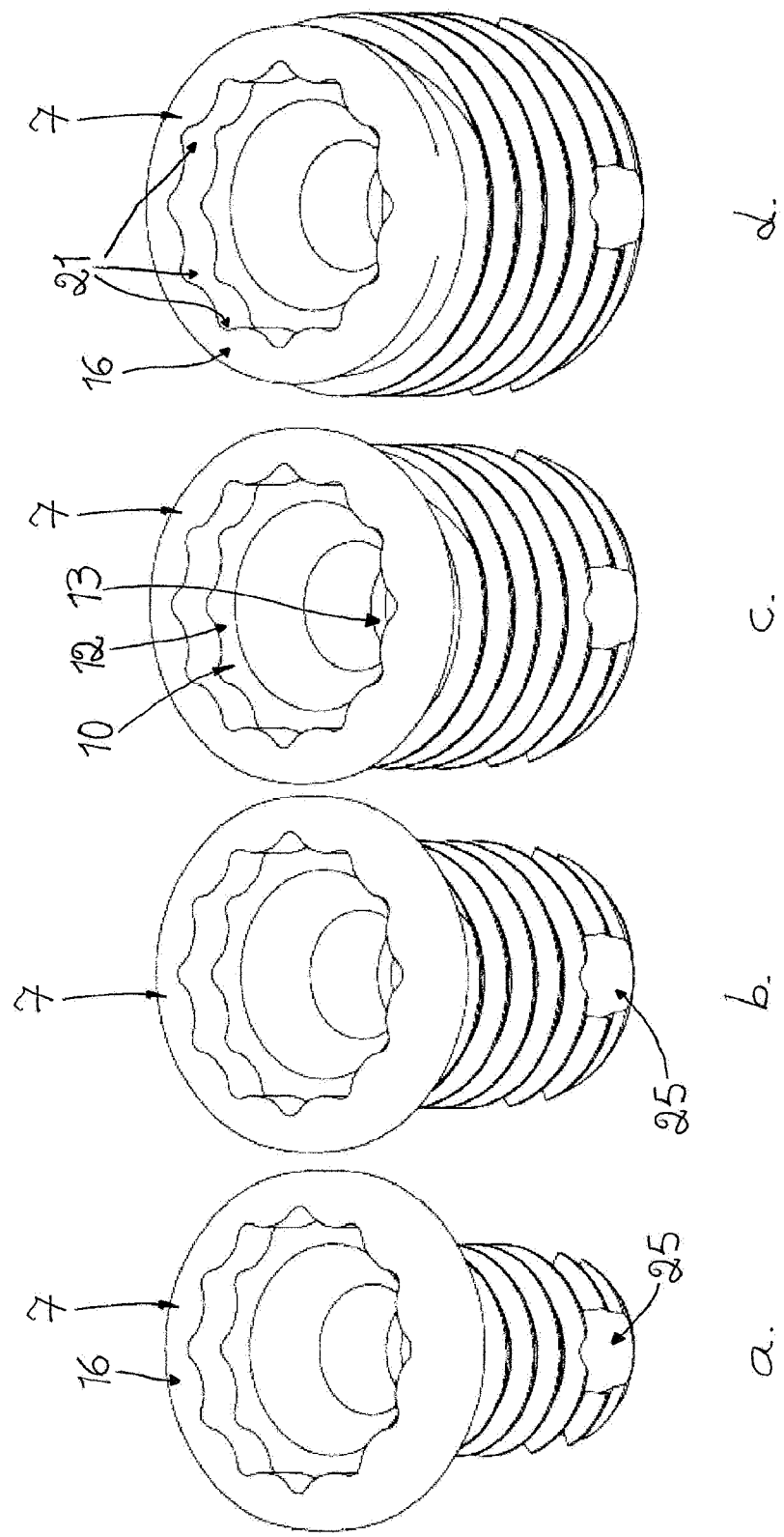

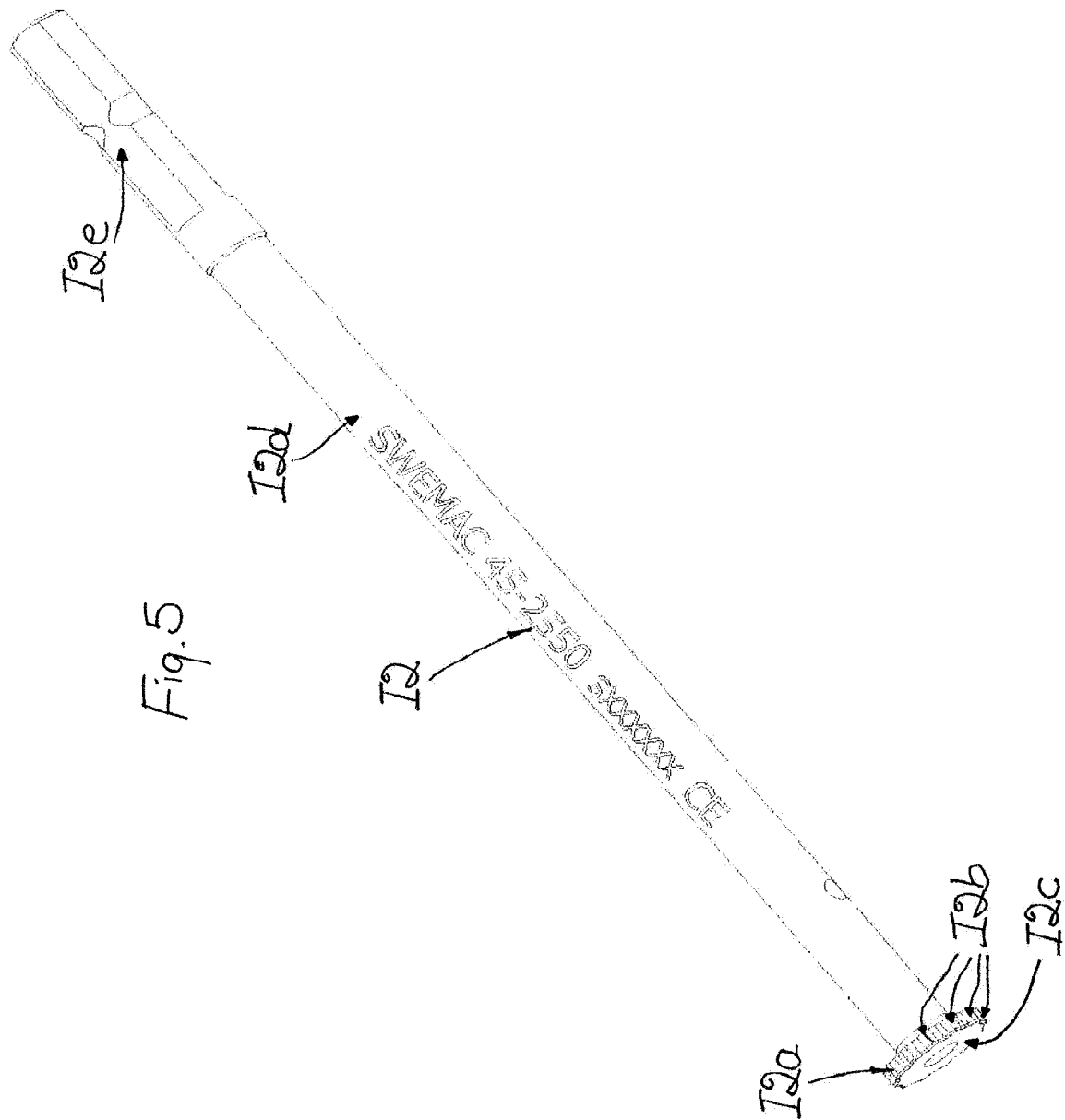

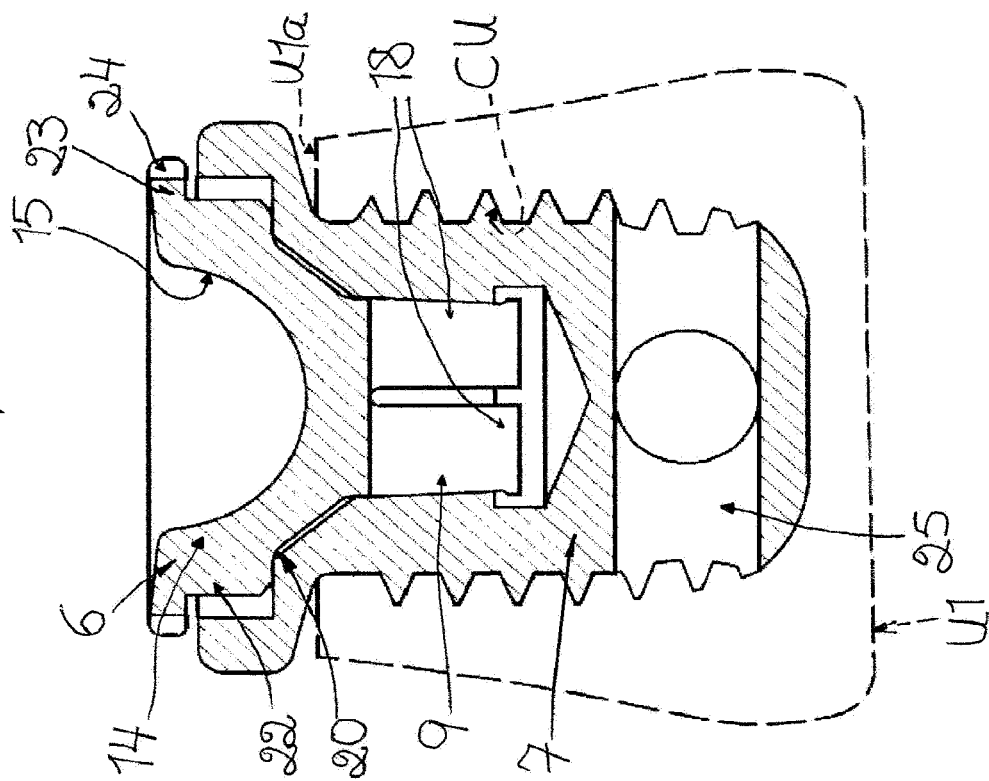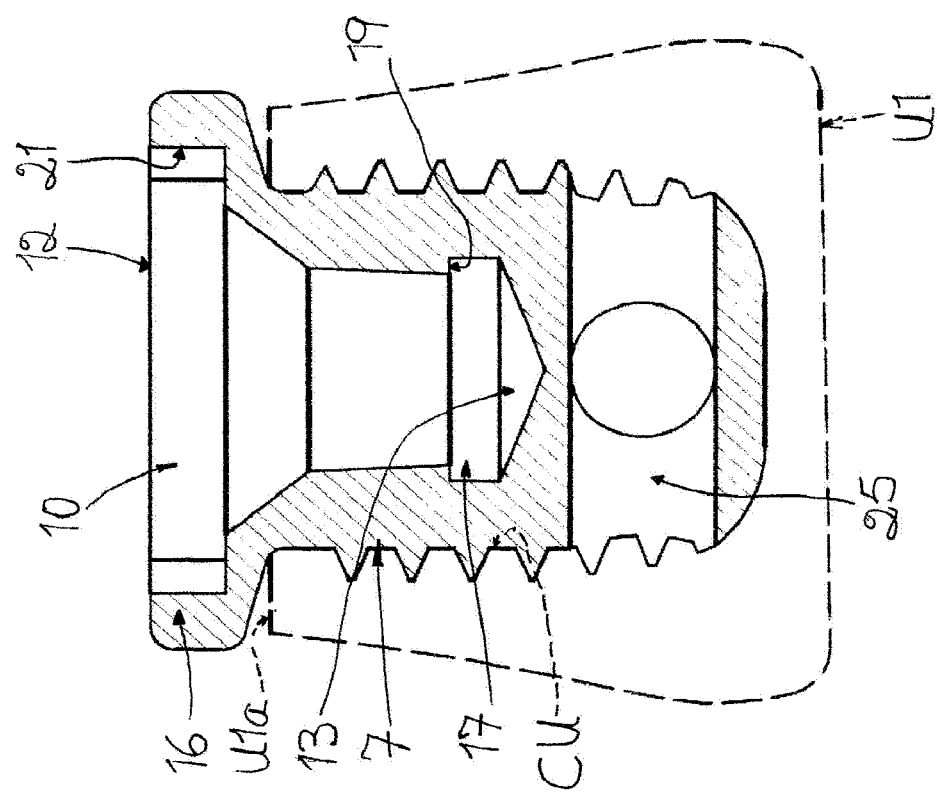

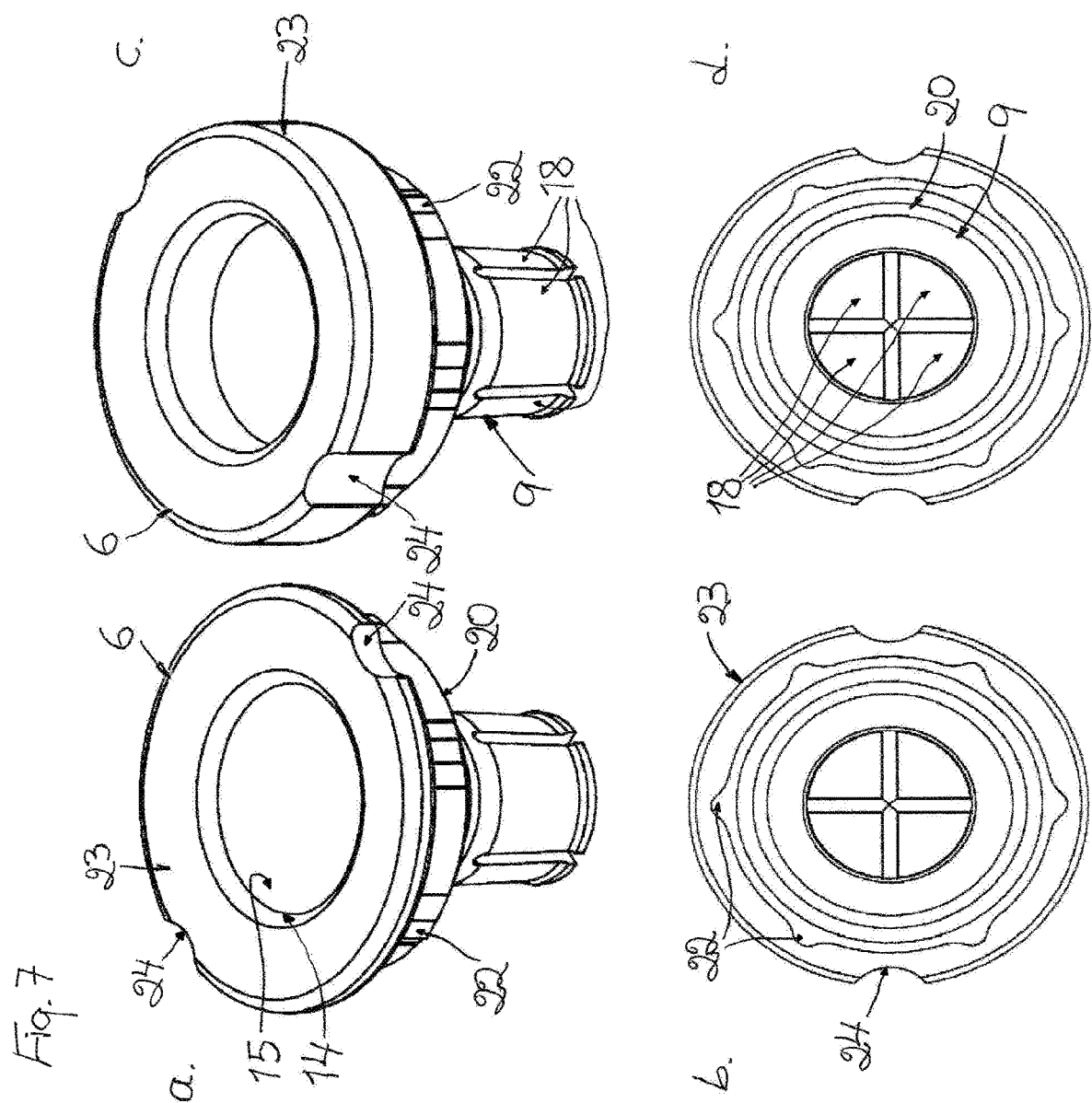

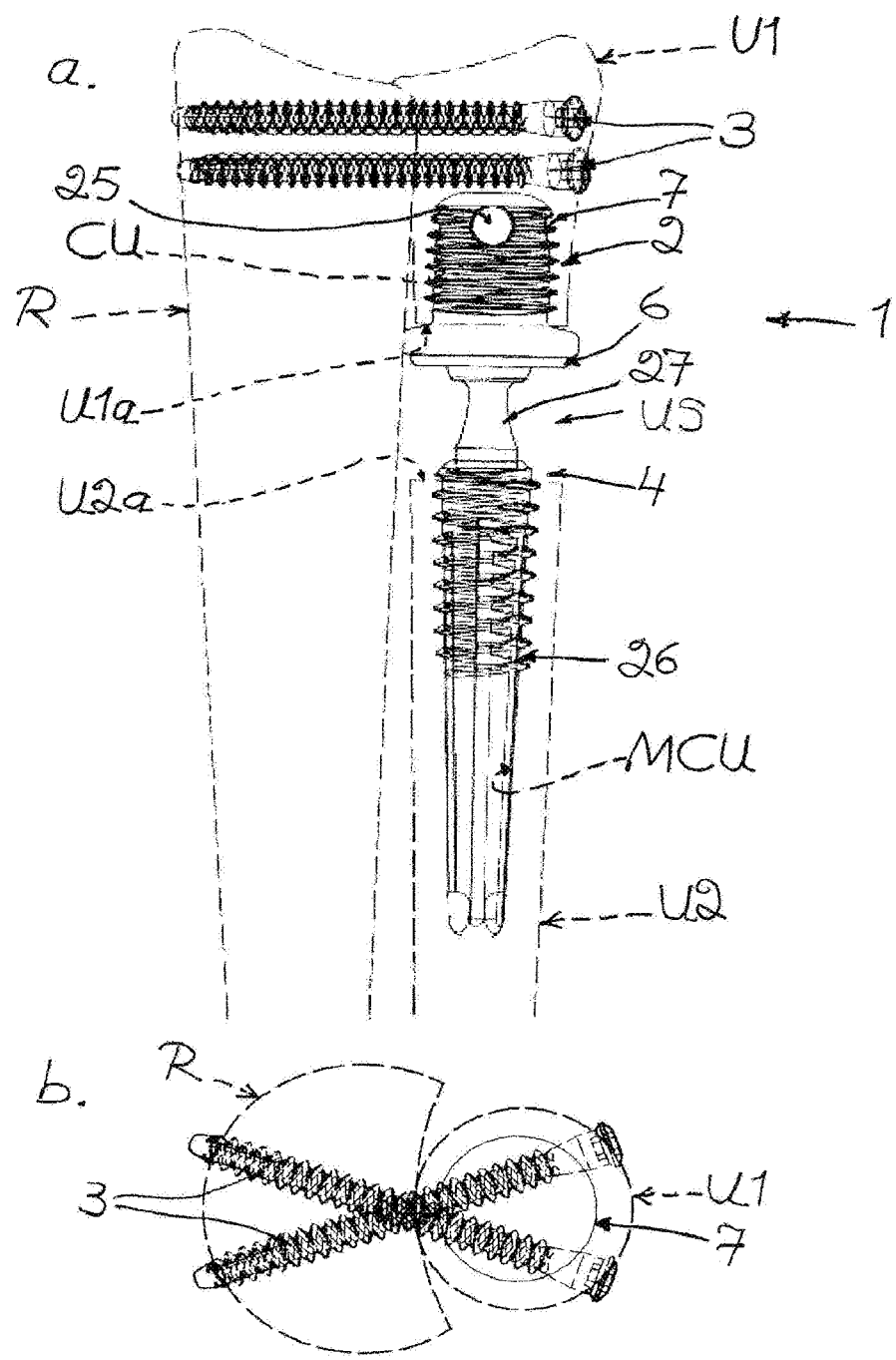

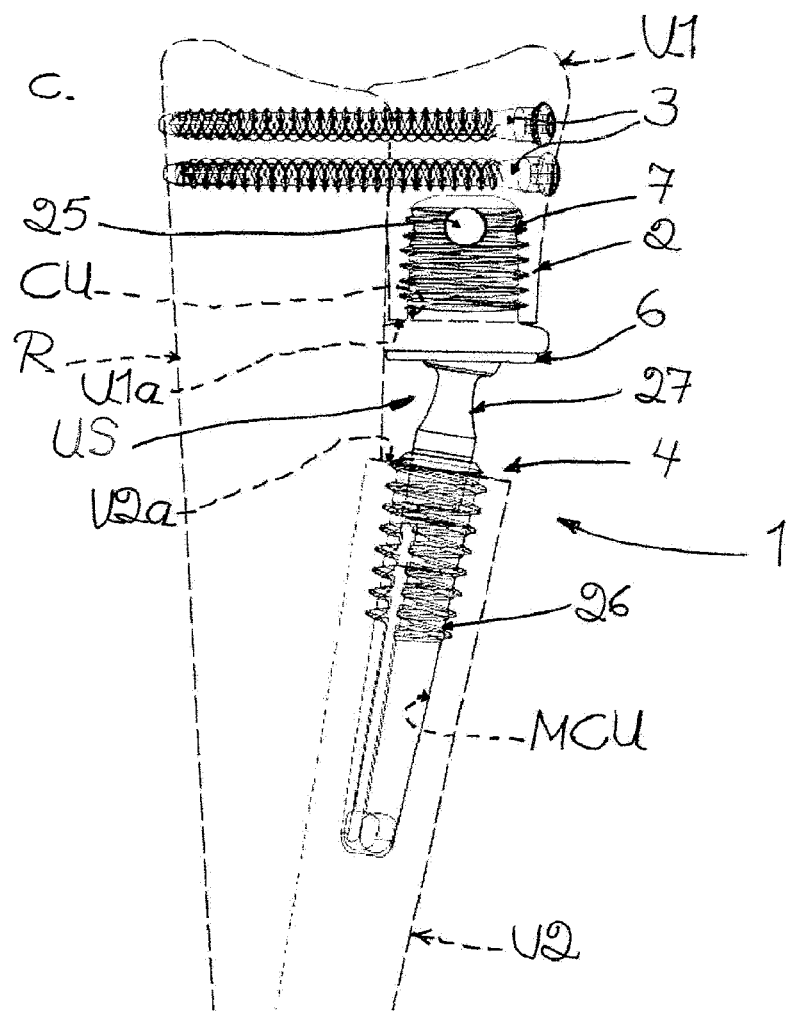

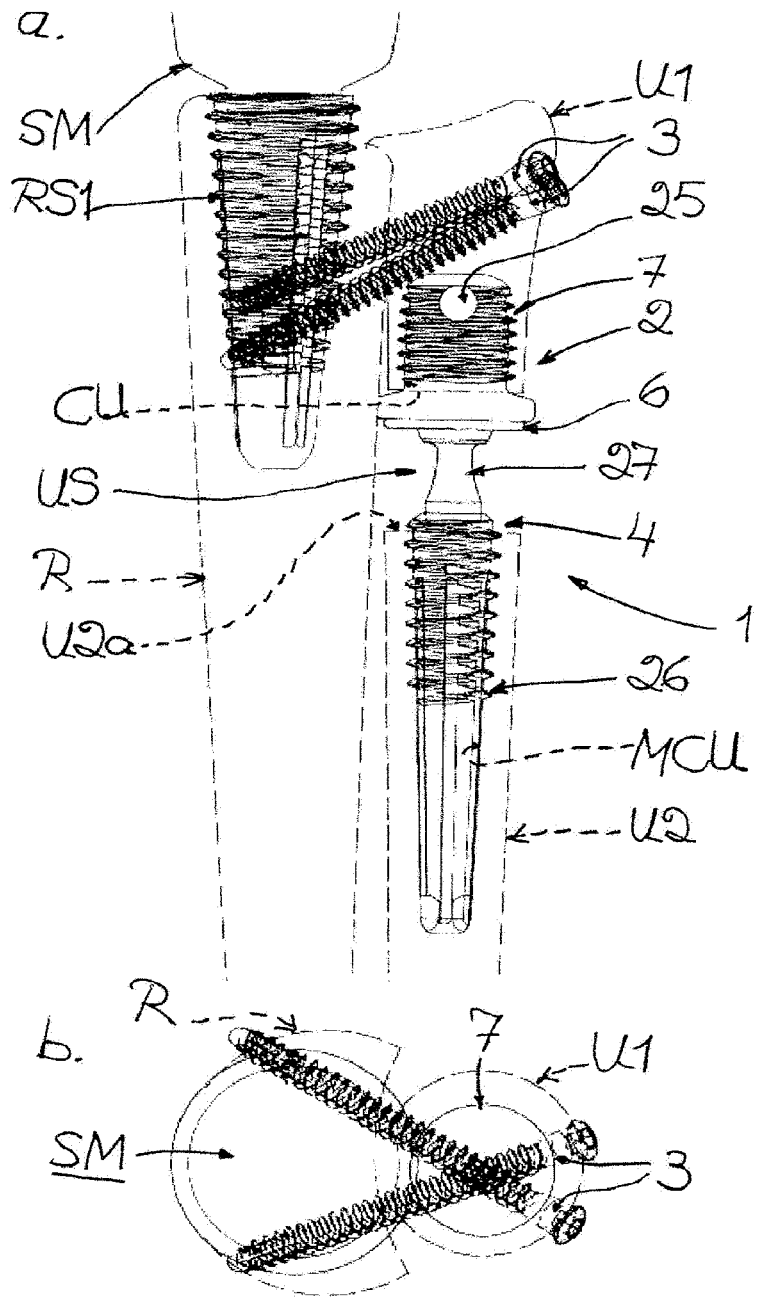

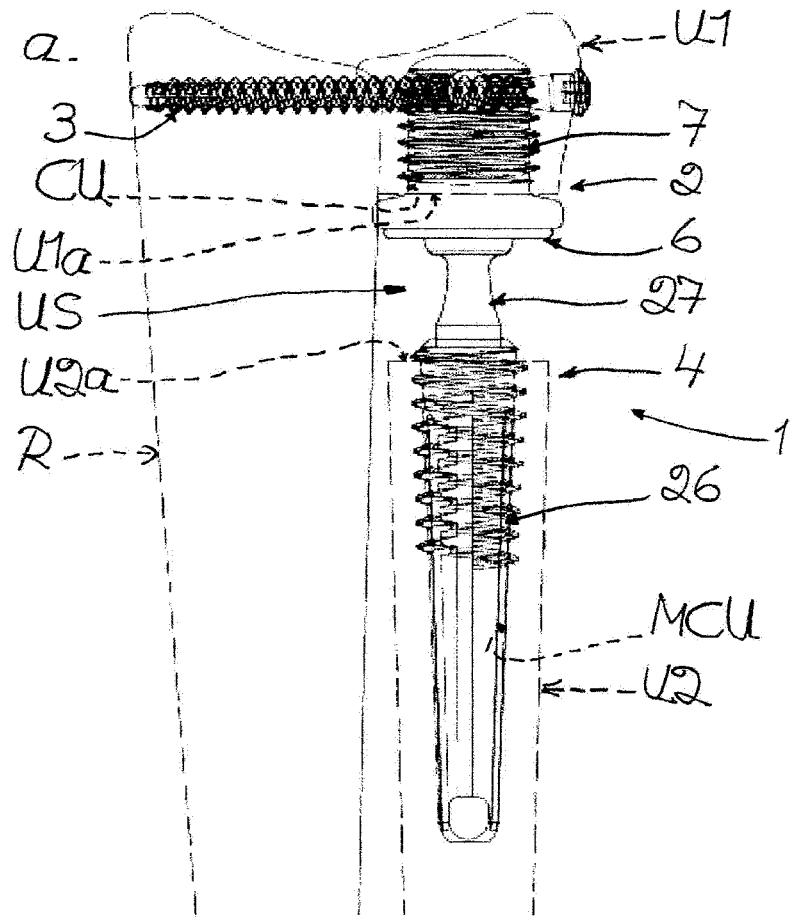
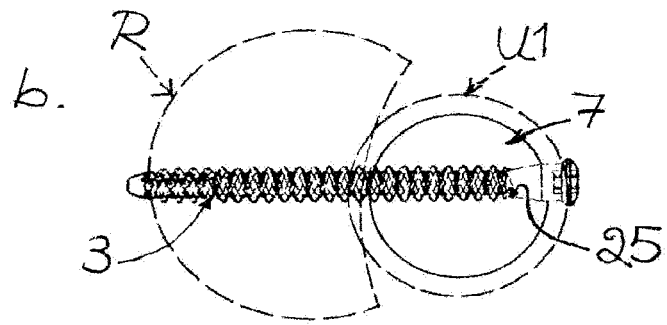

PROSTHESIS FOR RECONSTRUCTION OF DISTAL AND PROXIMAL RADIOULNAR JOINTS

RELATED APPLICATION

This application is a national stage entry of PCT/EP2016/076075, filed Oct. 28, 2016, the subject matter, of which is incorporated herein by reference in its entirety.

TECHNICAL FIELD

The present invention relates to a prosthesis for reconstruction of a distal radioulnar joint after resection of a part of the ulna close to a distal end portion thereof.

The present invention also relates to use of said prosthesis for reconstruction of a proximal radioulnar joint after resection of a part of the radius close to a proximal end portion thereof.

BACKGROUND OF THE INVENTION

Distal radioulnar prostheses are already known from e.g. EP 1 191 908 B1 and U.S. Pat. No. 5,108,444 A.

The forearm of the human body comprises two major bones, namely the radius and the ulna. In the natural position without a prosthesis, the distal end of the ulna and the distal end of the radius are not rigidly coupled to one another. These ends are located more or less separately alongside one another and the distal end of the smaller ulna is kept in place relative to the distal end of the radius by the triangular fibrocartilaginous complex, TFC. On moving the wrist and the hand, the ulna and radius are thus able to execute fairly complex movements or, in other words, have a high freedom of movement relative to one another. The ulna and radius can move relative to one another in the longitudinal direction. The ulna and radius can turn relative to one another e.g. in the sense that the ulna and radius from an initial position in which they run parallel to one another (supination) come into a position in which they cross one another (pronation) or in the sense that the ulna rotates about its longitudinal axis and the radius rotates about the ulna. The types of movement which the ulna and radius, particularly at the distal ends thereof, are able to perform, are known per se to a skilled person and will therefore not be described in further detail here.

There are many reasons which can necessitate reconstruction of a distal radioulnar joint, e.g. a fracture, a disease, a congenital abnormality or an abnormality as a result of surgery or trauma. Another cause is e.g. irritation due to pressure exerted on the bones.

In order to keep the freedom of movement of the ulna and radius intact as far as possible, it is known to replace the distal end portion of the ulna by an ulnar head prosthesis and holding it alongside the distal radius by means of an artificial fitted band. The relative movement of the ulna and radius in the longitudinal direction can be maintained in this way, but the joint has no stability.

The distal radioulnar joint prostheses of EP 1 191 908 B1 and U.S. Pat. No. 5,108,444 A are two different attempts to improve the freedom of movement of the distal ulna relative to the distal radius and keep it intact as far as possible. The distal radioulnar joint prostheses are thereby both configured to replace the distal end portion of the ulna and mechanically connect the distal end of the radius to the remaining part of the ulna.

A drawback with these prior art distal radioulnar joint prostheses however, is that the triangular fibrocartilaginous complex, TFC or TFCC, is resected with the distal end portion of the ulna. The TFC is important in load transmission across the ulnar aspect of the wrist. The TFC transmits and absorbs compressive forces. It is also a major stabilizer when it comes to control the rotation of the forearm by giving a strong but flexible connection between, inter alia, the distal radius and the distal ulna. The connection between the distal radius and the distal ulna maintains the congruency of the distal radioulnar joint. The ligaments support the joint through its arc of rotation and have accordingly influence on pronation and supination.

Several techniques of partial resection of the distal end portion of the ulna while preserving the ulnar styloid and the ligaments inserting at its base have been described. These techniques however, frequently fail to restore normal joint stability.

One attempt to preserve the TFC and the function thereof as well as the entire distal end portion of the ulna is known as the Sauvé-Kapandji technique. Here, a part of the ulna close to the distal end portion thereof is resected and the distal end portion of the ulna is immovably locked to the radius. Thus, the function of the TFC is maintained, but the remaining part of the ulna proximally of the distal end portion thereof is "hanging free", providing painful instability to the forearm.

SUMMARY OF THE INVENTION

The object of the present invention is to provide a distal radioulnar joint prosthesis which is configured to allow substantial preservation of the triangular fibrocartilaginous complex, TFC, and maintenance of much of the function thereof and yet further improve the freedom of movement of the distal ulna and the distal radius and thus, of the entire ulna and the entire radius relative to one another and keep it intact as far as possible. Normal stability to the joint and thus, to the forearm is substantially restored.

This is arrived at by means of a distal radioulnar joint prosthesis which according to the invention as defined in claim 1 comprises a first prosthesis member, one or more fixation means and a second prosthesis member. The first prosthesis member is configured for fixation to the distal end portion of the ulna. The fixation means is/are configured to extend into the radius via said distal end portion of the ulna for immovably locking said distal end portion of the ulna to the radius. The first prosthesis member will thereby also be locked to the radius. The second prosthesis member is configured for fixation to the ulna proximally of a space which is defined between the distal end portion of the ulna and the ulna proximally of said space by the resection of the part of the ulna close to said distal end portion of the ulna. The second prosthesis member is also configured to extend into said space for being joined with the first prosthesis member in a manner which allows said first and second prosthesis members to at least pivot and rotate relative to each other.

By not resecting the distal end portion of the ulna and thus, the TFC, and instead removing or resecting a part of the ulna close to said distal end portion of the ulna and connect said distal end portion to the remaining part of the ulna via the prosthesis according to the invention, the TFC is preserved and the functions thereof maintained. By additionally bringing together the first and second prosthesis members in a manner which allows them to at least pivot and rotate relative to each other, the freedom of movement of the ulna and radius relative to one another is substantially intact.

As indicated above, said prosthesis can be used also for reconstruction of a proximal radioulnar joint, whereby the first prosthesis member is configured for fixation to the proximal end portion of the radius, whereby the fixation means is/are configured to extend into the ulna via said proximal end portion of the radius for immovably locking said proximal end portion of the radius to the ulna such that the first prosthesis member is also locked to the ulna, whereby the second prosthesis member is configured for fixation to the radius distally of a space which is defined between the proximal end portion of the radius and the radius distally of said space by the resection of the part of the radius close to said proximal end portion of the radius, and whereby the second prosthesis member is also configured to extend into said space for being joined with the first prosthesis member in a manner which allows said first and second prosthesis members to at least pivot and rotate relative to each other.

This is possible while similar problems as at the distal radioulnar joint can occur at the proximal radioulnar joint. A similar solution is therefore close at hand, such that the ligaments and most of the function thereof at the proximal radioulnar joint can be preserved and stability to the joint restored.

Preferred embodiments of the present invention are set forth in the appended dependent claims, in the following description and in the drawings.

BRIEF DESCRIPTION OF THE DRAWINGS

The present invention will be further described below by means of a non-limiting example thereof with reference to the accompanying drawings, in which

FIG. 3 is a schematic perspective view of an instrument for use during resection of a part of the ulna;

FIG. 4a-d are a schematic perspective views of four different embodiments of a mounting portion of a first prosthesis member of the prosthesis according to FIGS. 1 and 2;

FIG. 5 is a schematic perspective view of an instrument for use during fixation of the mounting portion of the first prosthesis member in a distal end portion of the ulna after resection;

FIG. 6 is a schematic sectional view of the mounting portion of the first prosthesis member after fixation in the distal end portion of the ulna;

FIG. 7a-d is a schematic perspective view and a plan view respectively, of two different embodiments of a socket portion of the first prosthesis member of the prosthesis according to FIGS. 1 and 2;

FIG. 8 is a schematic sectional view of the socket portion of the first prosthesis member after insertion into the mounting portion of said first prosthesis member;

FIG. 10a-b is a schematic side view and a plan view respectively, of the prosthesis after implantation and after fixation of the distal end portion of the ulna and the first prosthesis member to the radius in a first manner and with the ulna and the radius running substantially in parallel to one another (supination);

FIG. 10c is a schematic side view of the prosthesis according to FIG. 10a-b, but with the ulna and the radius crossing one another (pronation);

FIG. 11a-b is a schematic side view and a plan view respectively, of the prosthesis after implantation and after fixation of the distal end portion of the ulna and the first prosthesis member to the radius in a second manner;

FIG. 12a-b is a schematic side view and a plan view respectively, of the prosthesis after implantation and after fixation of the distal end portion of the ulna and the first prosthesis member to the radius in a third manner.

It should be noted that the accompanying drawings are not necessarily drawn to scale and that the dimensions of some features of the present invention may have been exaggerated for the sake of clarity.

DETAILED DESCRIPTION OF PREFERRED EMBODIMENTS

The present invention will now be exemplified by a preferred embodiment thereof. It should however be realized that this embodiment is included in order to explain principles of the invention and not to limit the scope of the invention defined by the appended claims.

Figure 1:
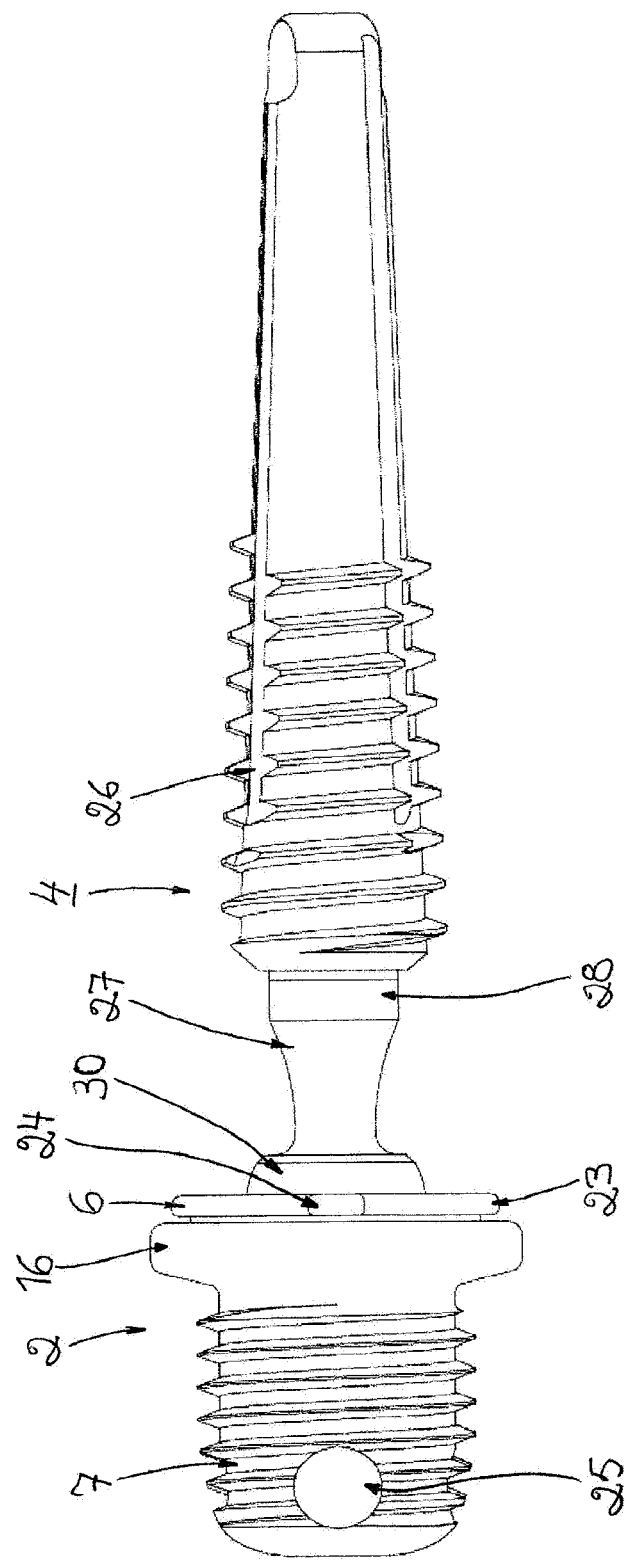
FIG. 1 is a schematic side view of a preferred embodiment of the first and second prosthesis members of a prosthesis for reconstruction of a distal radioulnar joint according to the invention.
Figure 2:
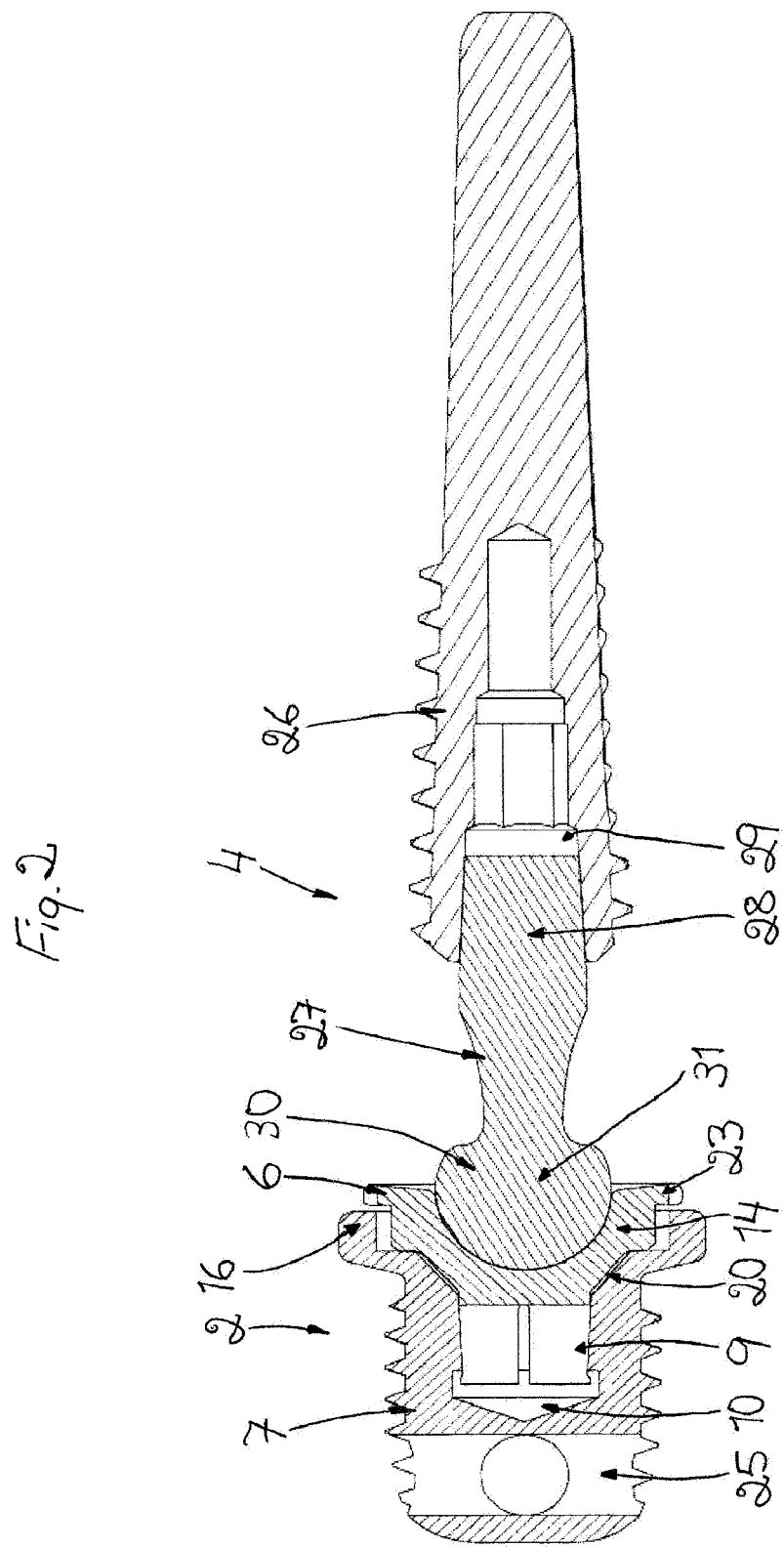
FIG. 2 is schematic sectional view of the preferred embodiment of the first and second prosthesis members of the prosthesis for reconstruction of a distal radioulnar joint according to the invention.

Thus, as already mentioned above, the present invention relates to a prosthesis for reconstruction of a distal radioulnar joint after resection of a part of the ulna close to a distal end portion thereof. Resection can be carried through by means e.g. of the instrument I1 illustrated in FIG. 3. The instrument I1, which is attached to the ulna during the resection, is configured with grooves I1a forming guides for a saw S. An example of the prosthesis members of the prosthesis according to the invention is illustrated in FIGS. 1 and 2. The length of the resected part of the ulna is preferably about 5 to 20 mm.

The distal radioulnar joint prosthesis 1 comprises generally a first prosthesis member 2, one or more fixation means 3 and a second prosthesis member 4. Instead of resecting the distal end portion U1 of the ulna, which has been the most common practice, said distal end portion is preserved and, as mentioned, a part of the ulna close to the distal end portion thereof is resected. The length of the distal end portion U1 of the ulna may after removal of the resected part be about 15 to 25 mm. The first prosthesis member 2 is according to the invention configured for fixation to the distal end portion U1 of the ulna, inside said distal end portion, on the outside thereof or both. The fixation means 3 are configured to extend into the radius R via said distal end portion U1 of the ulna for compressing said distal end portion of the ulna and the radius, preferably after removal of cartilage tissue therebetween, and immovably locking said distal end portion of the ulna to the radius. The first prosthesis member 2 is thereby also, at least indirectly, locked to the radius. The second prosthesis member 4 is configured for fixation to the ulna proximally of a space US which is defined between the distal end portion U1 of the ulna and the remaining part of the ulna U2 proximally of said space by the resection of the part of the ulna close to said distal end portion of the ulna, i.e. the space corresponds in other words substantially to the resected part of the ulna. The second prosthesis member 4 may be fixed to said proximal part U2 of the ulna inside said proximal part, on the outside thereof or both. The second prosthesis member 4 is also configured to extend into said space US for being joined with the first prosthesis member 2 in a manner which allows said first and second prosthesis members to at least pivot and rotate relative to each other, thereby letting the radius R together with the distal end portion U1 of the ulna and the ulna U2 proximally of said space US between said distal end portion U1 of the ulna and said proximal part U2 of the ulna to perform substantially "normal" pronation and supination movements.

The first prosthesis member may be configured in many different ways in order to meet the requirements thereon and in order to fulfil its functions.

In the illustrated preferred embodiment, the first prosthesis member 2 comprises to this end a socket portion 6 and a mounting portion 7 which is configured for fixation of said socket portion in a cavity CU in the surface U1a of the distal portion U1 of the ulna defined by the resected part of the ulna close to said distal portion, i.e. the surface of the distal end portion facing the space US and the ulna U2 proximally of said space. The cavity CU is formed by inserting a guide wire into the distal end portion U1 of the ulna from said surface U1a thereof and then drill the cavity by means of a drill which is threaded onto the guide wire. Fixation of the mounting portion 7, and thereby of the socket portion 6, in the cavity CU in the surface U1a of the distal portion U1 of the ulna can be accomplished in various ways, e.g. as in the illustrated preferred embodiment by configuring the mounting portion at least partly with an external thread such that said mounting portion can be screwed into said cavity. The thread is preferably self-tapping. After fixation, a part of the socket portion 6 may, as illustrated in the drawings, protrude into the space US between the distal end portion U1 of the ulna and the proximal part U2 of the ulna.

The first prosthesis member 2, i.e. the socket portion 6 and the mounting portion 7 thereof, may be made in one piece or, as in the illustrated preferred embodiment, constitute separate members. By providing the socket portion 6 and the mounting portion 7 as separate members, it is possible, if desired, to manufacture said members in different suitable materials based on the purposes of said members and the requirements thereon. Thus, the socket portion 6 can be made of e.g. a plastic material such as PEEK (polyetheretherketon) and the mounting portion 7 of e.g. a metal or metal alloy such as Ti6Al4V. The metal or metal alloy may be covered with a suitable material which is more compatible with the human body in order to further improve osseointegration.

The mounting portion of the first prosthesis member 2 may as in the illustrated preferred embodiment be configured as a (distal) screw-like part 7 with self-tapping threads. The screw-like part 7 is screwed into the cavity CU in the distal end portion U1 of the ulna (FIG. 6) and the socket portion 6 may have a mounting pin 9 which is insertable into a hole 10 in the screw-like part 7 for attaching the socket portion thereto (FIG. 8). The hole 10 in the screw-like part 7 extends into said part as a depression and is axially centered therewith. The hole 10 has a shape which from the opening 12 thereto is tapering conically towards the bottom 13 of said hole. The conicity may be unchanged in the longitudinal direction of the hole or may vary in the longitudinal direction of the hole.

The socket portion 6 comprises, beyond the mounting pin 9, a socket 14 which defines a depression or cup-shaped concave joint or guide surface 15. The mounting pin 9 projects in an axial direction from the outer side of the socket 14. The mounting pin 9 may taper conically from the socket 14. The shape and size of the mounting pin 9 and the shape and size of the hole 10 in the screw-like part 7 may be selected such that they form a press fit by moving them together in an axial direction, i.e. such a connection which permits bringing the socket portion 6 and the screw-like part 7 to attach to each other by pressing them together. The shape and size of the mounting pin 9 on the socket portion 6 and the shape and size of the hole 10 in the screw-like part 7 may also be selected such that they attach to each other in another way, which is described in more detail below.

The diameter of the screw-like part 7 is chosen relative to the cross-sectional area of the distal end portion U1 of the ulna such that the screw-like part fits with practically all relevant sizes of distal end portions and in order to provide for maximum fixation of the screw-like part in the cortical bone of said distal end portions. The diameter of the screw-like part 7 to be used will thereby preferably vary between 6 and 12 mm. Screw-like parts 7 of four different diameters are illustrated in FIG. 4a-d. The length of the distal screw-like parts 7 may vary between e.g. 10 to 20 mm. By the use of a properly dimensioned screw-like part 7, the moments generated during loading are kept at a minimum, since these moments can be spread over a relative large surface of great strength. Sufficient room in particularly the opening 12 to the hole 10 for the socket 14 in the socket portion 6, i.e. room for a socket having a diameter of about 6 mm, is provided by configuring screw-like parts of all said diameters with a collar 16 having a diameter of preferably 10 or 12 mm around said opening 12. The collar 16 may be configured with threads (not shown) for screwing also said collar into the surface U1a of the distal end portion U1 of the ulna in order to thereby further improve the fixation of the screw-like part 7 in said distal end portion of the ulna. Rotation of the first prosthesis member 2 is prevented. The center of movement for a ball element fitting into the socket 14 is found relatively far down in the distal end portion U1 of the ulna. The risk for luxation is thereby reduced.

The hole 10 in the screw-like part 7 and the mounting pin 9 of the socket portion 6 are configured with complementary portions for fastening or fixation of the socket portion in the screw-like part.

Depending on particularly the type of socket portion 6, these portions may, as indicated above, be configured to form a press fit such that the socket element and the screw-like part 7 by means of a press fit are brought to attach to each other. This is true particularly if both members 6, 7 are made of metal or a metal alloy, e.g. if the socket portion 6 is also made of a CoCrMo-alloy or Ti6Al4V instead of a plastic material.

However, if the socket portion 6 consists of e.g. a plastic material such as PEEK, which might be reinforced with carbon fibers, the complementary attachment portions may be configured differently, as indicated above. A socket portion of PEEK is illustrated in the drawings, particularly in FIGS. 7a-d and 8. At this latter embodiment, the hole 10 in the screw-like part 7 may at the bottom 13 be provided with a snap-in attachment 17 for the mounting pin 9 of the socket portion 6 and the mounting pin is configured with snap-in portions 18 which engage the snap-in attachment in the hole in said screw-like part. As is apparent from the drawings, the snap-in attachment 17 in the hole 10 is defined by a smaller extension of the hole in the parts thereof close to the bottom 13 of the hole, and the snap-in portions 18 on the mounting pin 9 are configured as hook-like parts. From the drawings it is also apparent that the mounting pin 9, in order to permit a snap-in connection thereof in the hole 10, is divided into four members with each a hook-like part. The mounting pin 9 may of course also be divided into less or more than four members and each such member may in turn have more than one hook-like part. The snap-in portions 18 configured as hooks on the mounting pin 9 of the socket portion 6, are brought together during insertion of the mounting pin in the hole 10, but move apart in the extended part of the hole and prevent retraction of the socket portion by engaging the surface 19 defined by said extension and facing the bottom 13 of the hole.

The hole 10 in the screw-like part 7 and a part 20 of the socket portion 6 defining the socket 14, are also configured with complementary portions which prevent rotation of the articulating socket element relative to the screw-like part.

At the preferred embodiment illustrated in the drawings, particularly in FIGS. 4a-d and 7a-d, the hole 10 in the screw-like part 7 is to this end on the inside of the opening 12 thereto provided with at least one recess 21 and the socket portion 6 has externally on the part 20 defining the socket 14 at least one protrusion 22 which engage the recess in the screw-like part. As is apparent from the drawings, said at least one recess on the inside of the opening 12 to the hole 10 may be configured as a number of recesses 21 uniformly distributed along said inside. The number of recesses 21 may vary and be more or less than twelve. From the drawings it is apparent that said at least one protrusion on the part 20 may comprise six protrusions 22 uniformly distributed peripherally on the outside of said portion and having a curved side with substantially the same radius as the recesses 21. The number of protrusions 22 may also vary and be more or less than six, but not more than the number of recesses 21.

The socket portion 6 may comprise, except for the mounting pin 9 and except for the part 20 defining the socket 14 and having at least one protrusion 22, a collar 23 on said part. The object of this collar 23, which, when the socket portion 6 is inserted into the screw-like part 7, protrudes a little bit over said screw-like part of a metal or metal alloy, is, inter alia, to permit restoration without metalosis at a possible luxation or dislocation. The collar 23 will accordingly also protrude a small distance into the space 5 between the distal end portion U1 of the ulna and the proximal part U2 thereof. As is apparent from FIGS. 7a and 7c, the collar 23 may vary in height for reasons described below. Recesses 24 for a tool for handling the socket portion 6 during surgery may be provided on the outer periphery of the collar 23. At the illustrated embodiments, the collar 23 has two recesses 24 located diametrically opposite each other.

The recess or recesses 21 in the hole 10 in the screw-like part 7 on the inside of the opening 12 thereto, may also be used to permit insertion into said recess or recesses of a driving portion I2a of a driving tool I2 for attachment by screwing of the screw-like part to the distal end portion U1 of the ulna. Such a driving instrument is illustrated in FIG. 5. It is of course possible to configure the screw-like part 7 with one or more other recesses for fixation thereof by screwing by means of a driving instrument and the driving instrument may be designed otherwise than the driving instrument of FIG. 5. The driving portion I2a of the driving instrument I2 however, is in the embodiment of FIG. 5 configured with protrusions I2b which fit into the recesses 21. The protrusions I2b, the number of which in the illustrated embodiment corresponds to the number of recesses 21, but which also may be less than that, are provided on a plate-like member I2c of the driving portion which is attached to one end of an elongated shaft I2d of the driving instrument I2. The free end of the shaft I2d, opposite to the shaft end with the driving portion I2a, may be configured with grip portions I2e for cooperation with a rotary movements generating tool, e.g. a drilling machine, or be configured with a handle or grip portions for cooperation with a handle for manual rotation of the driving instrument. By rotating the driving instrument I2 after insertion of the driving portion I2a thereof into the opening 12 to the hole 10 and after bringing the protrusions I2b into engagement with the recesses 21, the screw-like part 7 can be fixed to the distal end portion U1 of the ulna by screwing.

Alternatively, if the size of the screw-like part permits it, the bottom 13 of the hole 10 may also be configured as or with a groove, e.g. a hexagon groove, for attachment by screwing of the screw-like part by means of a driving instrument in the shape of e.g. a hexagon wrench. The groove in the bottom 13 of the hole 10 may of course also be shaped otherwise and so may the driving instrument.

As with the first prosthesis member, the fixation means may also be configured as well as arranged in many different ways in order to meet the requirements thereon and in order to fulfil its functions.

In the illustrated embodiment according to FIG. 12a-b, there is one fixation means 3, but there may also be e.g. two fixation means as in FIG. 10a-c and FIG. 11a-b, or even three or more fixation means. If two or more fixation means 3 are used, they may run through the distal end portion U1 and into the radius R in parallel or in non-parallel directions, i.e. at an angle relative to each other to thereby improve locking of the distal end portion of the ulna to the radius. Angular or cross-linked fixation means 3 may directly or indirectly lock the first prosthesis member 2 to the radius R and may further allow for use where e.g. a screw forming part of another implant or prosthesis, e.g. a wrist prosthesis, is situated in the radius, e.g. a radius screw RS1 and a socket member SM from a wrist arthroplasty (FIG. 11a-b). Thus, the embodiment of FIG. 11a-b allows simultaneous fixation of a wrist prosthesis and a distal radioulnar joint prosthesis according to the present invention. As illustrated in FIG. 11a-b, the cross-linked fixation means 3 may also run obliquely in proximal direction. The fixation means 3 may be bone screws with a threaded fixing portion as in the illustrated embodiment for fixation in at least the radius R, or may be bone nails. Also, if e.g. three fixation means 3 in the form of bone screws are used, an intermediate bone screw may be a compression screw and the two bone screws on both sides of the compression screw may be locking screws.

Alternatively, if desired, the fixation means 3 may also lock the first prosthesis member 2 in the distal end portion U1 of the ulna to the radius R in a more direct manner (FIG. 12a-b). The first prosthesis member 2 or rather, the mounting portion 7 thereof, may to this end be configured with one or more through-holes 25 for the fixation means 3 (see particularly FIG. 4a-d and FIG. 12a-b). By the more direct locking of the first prosthesis member 2 to the radius R by means of the fixation means 3, said first prosthesis member is fixed also to the distal end portion U1 of the ulna even if the mounting portion 7 thereof is not configured with an external thread or as a screw-like part.

At the embodiments of FIG. 10a-c and FIG. 12a-b, it will be necessary to first let the distal radioulnar joint prosthesis 1 heal and form an arthrodesis between the distal end portion of the ulna and the radius and then remove the fixation means 3 before preparations for fixation of a wrist prosthesis can be initiated.

Finally, the second prosthesis member may also be configured in many different ways in order to meet the requirements thereon and in order to fulfil its functions.

Figure 9:
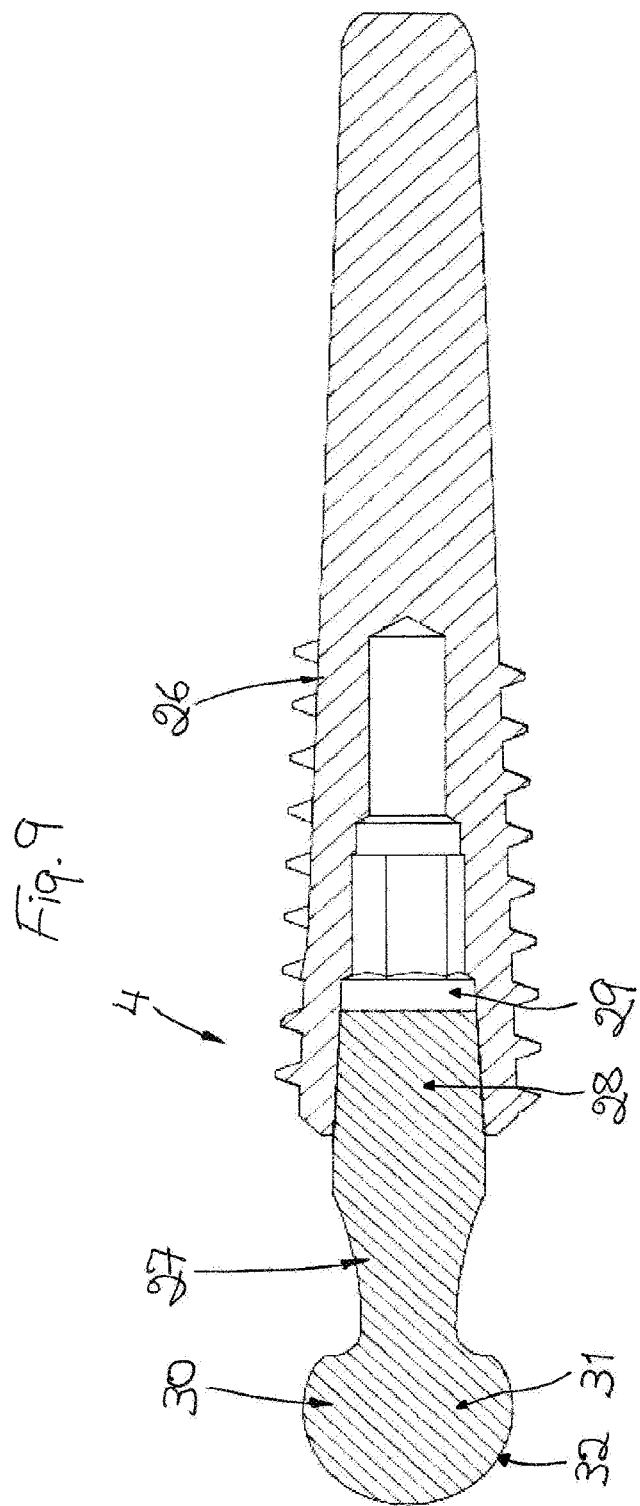
FIG. 9 is a schematic sectional view of a second prosthesis member after insertion of a head portion of said second prosthesis member into a mounting portion thereof.

In the illustrated embodiment, the second prosthesis member 4 comprises a mounting portion 26 which is configured for fixation in the marrow cavity MCU of the ulna U2 proximally of the space US which is defined between the distal end portion U1 of the ulna and said proximal part of the ulna, i.e. the cavity which opens into and faces said space and the surface U1a of the distal portion U1 of the ulna. Room for the mounting portion 26 in the marrow cavity MCU is provided by inserting a guide wire in said marrow cavity from the surface U2a facing the space US and the surface U1a of the distal end portion U1 of the ulna and then enlarge the marrow cavity by means of a drill which is threaded onto the guide wire. Fixation of the mounting portion 26 in the enlarged marrow cavity MCU of the ulna U2 proximally of the space US can be accomplished in various ways, e.g. as in the illustrated preferred embodiment by configuring the mounting portion at least partly with an external thread such that said mounting portion can be screwed into said marrow cavity. The mounting portion 26 may be completely screwed into the enlarged marrow cavity MCU or may extend somewhat into the space US between the distal end portion U1 of the ulna and the proximal part U2 of the ulna. The second prosthesis member 4 also comprises a head portion 27 which is configured to extend from the mounting portion 26 in said enlarged marrow cavity MCU and into the space US between the distal end portion U1 of the ulna and the ulna U2 proximally of said space for joining said second prosthesis member with the first prosthesis member 2. To accomplish this, the head portion 27 of the second prosthesis member 4 is at one end integral with the mounting portion 26 or alternatively configured with a mounting pin 28 which is insertable into a hole 29 in the mounting portion 26 for attachment thereto (FIG. 9) and, at the opposite free end, configured with a ball element 30 fitting into the socket 14 of the socket portion 6 of the first prosthesis member 2 such that the first and second prosthesis members can at least pivot and rotate relative to each other.

The second prosthesis member 4, i.e. the mounting portion 26 and the head portion 27 thereof, may as indicated be made in one piece or, as in the illustrated preferred embodiment, constitute separate members. By providing the mounting portion 26 and the head portion 27 as separate members, it is possible, if desired, to manufacture said members in different suitable materials based on the purposes of said members and the requirements thereon. Thus, the mounting portion 26 can be made of a metal or metal alloy such as Ti6Al4V and head portion 27 of another metal or metal alloy, e.g. CoCrMo. The former metal or metal alloy may be covered with a suitable material which is more compatible with the human body in order to further improve osseointegration.

The hole 29 in the mounting portion 26, which mounting portion also can be configured as a (proximal) screw-like part with preferably self-tapping threads, is preferably provided and configured conically in the same way as the hole 10 in the first screw-like part 7, but may also be configured in any other suitable way. The end of the head portion 27 fitting with the hole 29 in the mounting portion/proximal screw-like part 26 have a corresponding conical configuration. The length of the proximal screw-like part 26 is preferably about 25 to 35 mm.

The above-mentioned configuration of the first and second prosthesis members 2, 4 may also allow a certain relative movement of said prosthesis members substantially in the longitudinal direction of said first and second prosthesis members in order to facilitate pronation and supination of the forearm. The required relative movement is about 2 to 3 mm and can be compensated for by e.g. making the socket portion 6 and thus, the socket 14 a little bit higher than necessary for accommodating the ball element 30 such that an increased slack between said members is allowed without dislocation or luxation of the prosthesis 1 during movements of the first and second prosthesis members 2, 4 between positions corresponding to pronation and supination of the forearm. This can be accomplished by e.g. increasing the height of the collar 23 of the socket portion 6 (see FIG. 7c). As an alternative or in combination with the somewhat higher socket 14 of the socket portion 6, one can control the tension by means of which the ball element 30 of the head portion 27 is fitting into said socket, i.e. determine, when the forearm is in a position between pronation and supination, which length the head portion/ball element to be used shall have in order not to generate a too high pressure against the socket 14 in any position of the forearm between pronation and supination and thereby not risking e.g. breakage of the arthrodesis between the distal end portion of the ulna and the radius.

The ball element 30 comprises a substantially spherical ball 31 which defines a convex joint or guide surface 32 of such shape that it fits in the guide surface 15 of the socket 14 such that said guide surfaces 14, 32 can slide against each other and provide articulation of the joint. The mounting pin 28 on the head portion 27 extends in an axial direction from the ball element 30 and this mounting pin has preferably a corresponding conical shape as the mounting pin 9 on the socket portion 6, but may also be configured in any other suitable manner. The shape and size of the mounting pin 28 on the head portion 27 and the shape and size of the hole 29 in the mounting portion/proximal screw-like part 26 may be selected such that they by moving them together in an axial direction can form a press fit corresponding to the press fit between the socket element 6 and the distal screw-like part 7. The shape and size of the mounting pin 28 on the head portion 27 and the shape and size of the hole 29 in the proximal screw-like part 26 may also be selected such that they attach to each other in another way.

A more detailed description of how and in which order the various members 6, 7 and 26, 27 respectively, of the first and second prosthesis members 2, 4 of the distal radioulnar joint prosthesis are attached to the distal end portion U1 of the ulna and to the ulna U2 proximally of said distal end portion of the ulna and of the space US respectively, as well as to each other, and any additional instruments used therefor, is not given here.

It is obvious to a skilled person that the present invention can be modified and altered within the scope of the appended claims without departing from the idea and object of the invention. As such, the present invention should not be considered as limited by the embodiment thereof described above nor by the figures illustrating this embodiment. Rather, the full scope of the invention should be determined by the appended claims, with reference to the description and the drawings. Thus, as indicated, the number and size of the fixation means 3 may vary and so may the location thereof. The size and/or thickness of the first and second prosthesis members 2, 4 may also, as indicated, vary based on the anatomy of the patient and based on the size of the space US between the distal end portion U1 of the ulna and the ulna U2 proximally of said space, i.e. of the size of the resected part of the ulna and of how much e.g. the surfaces U1a, U2a facing said space of the remaining parts of the ulna and how said surfaces U1a, U2a engaged by the first and second prosthesis members have been shaped to fit therewith. It is within the scope of the invention possible to alternatively provide the first prosthesis member 2 for the distal end portion U1 of the ulna with a head portion which is either integrated with the mounting portion 7 thereof or constitutes a separate member which is configured for connection to said mounting portion and which is configured for extension into the space US which is defined between said distal end portion of the ulna and the ulna U2 proximally of said space, and to provide the second prosthesis member 4 for the ulna proximally of said space between said distal end portion of the ulna and said proximal part U2 of the ulna with a socket portion which also is either integrated with the mounting portion 26 thereof or constitutes a separate member which is configured for connection to said mounting portion. Thus, as indicated, the joint or connection of the first and second prosthesis members 2, 4 may be configured in many different ways. The entire prosthesis 1 may be made of e.g. titanium or PEEK or any other material which improves osseointegration. However, as indicated above, the prosthesis 1 can alternatively be made of e.g. a CoCr-alloy or any other suitable metallic or plastic material and the first and second prosthesis members 2, 4 may also be made of different materials.

Figure 13:
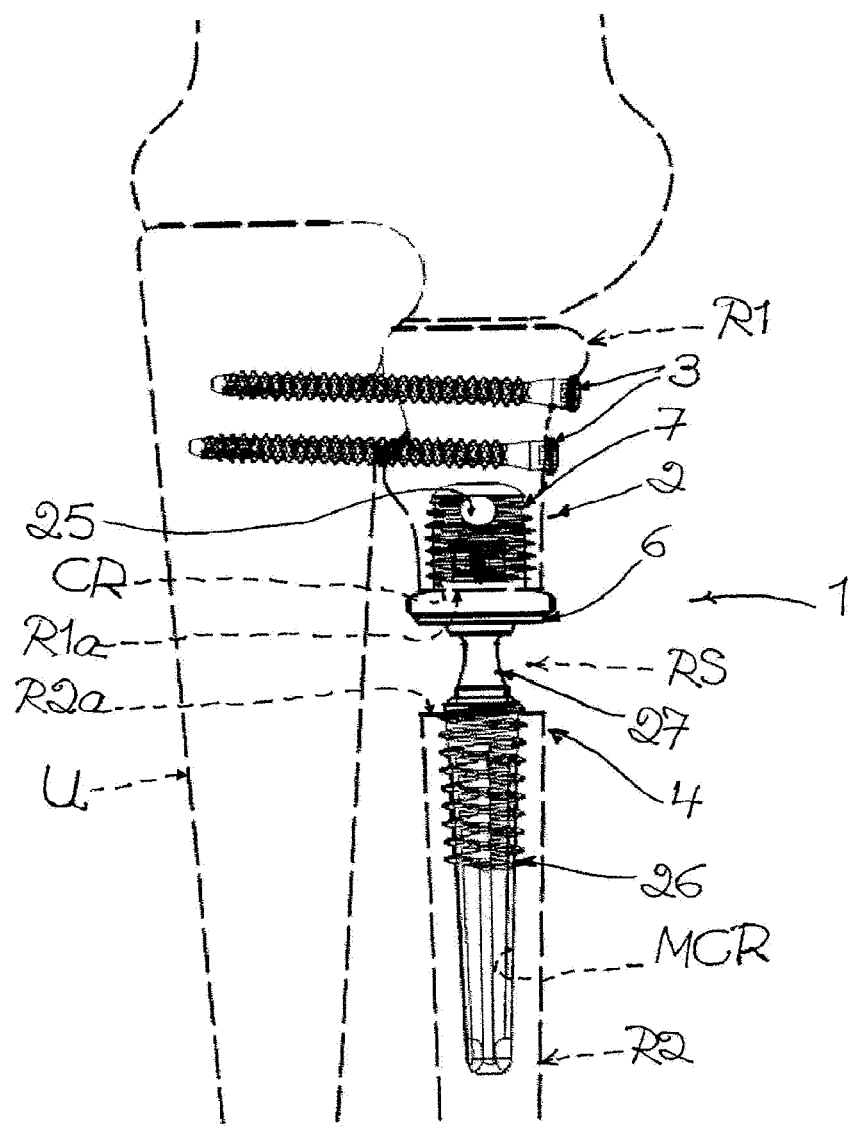
FIG. 13 is a schematic side view of the prosthesis of FIG. 10a after implantation and fixation of a proximal end portion of the radius and the first prosthesis member to the ulna for reconstruction of a proximal radioulnar joint.

As illustrated in FIG. 13, it is also within the scope of the present invention to use the prosthesis described above for reconstruction of a proximal radioulnar joint after resection of a part of the radius close to a proximal end portion thereof. Thereby, the first prosthesis member 2 is configured for fixation to the proximal end portion R1 of the radius, the fixation means 3 is/are configured to extend into the ulna U via said proximal end portion R1 of the radius for immovably locking said proximal end portion of the radius to the ulna U, the second prosthesis member 4 is configured for fixation to the radius distally of a space RS which is defined between the proximal end portion R1 of the radius and the radius R2 distally of said space by the resection of the part of the radius close to said proximal end portion of the radius, and the second prosthesis member 4 is also configured to extend into said space RS for being joined with the first prosthesis member 2 in a manner which allows said first and second prosthesis members to at least pivot and rotate relative to each other.

Accordingly, since the same prosthesis is used, the first prosthesis member 2 still comprises a socket portion 6 which is configured with a socket 14 and a mounting portion 7 which is configured for fixation of said socket portion in a cavity CR in the surface R1a of the proximal end portion R1 of the radius facing the space RS which is defined between proximal end portion R1 of the radius and the radius R2 distally of said space. The second prosthesis member 4 also still comprises a mounting portion 26 which is configured for fixation in the marrow cavity MCR of the radius R2 distally of said space RS between the proximal end portion R1 of the radius and the radius R2 distally of said space, and a head portion 27 which is configured to extend into said space RS for joining said second prosthesis member with said first prosthesis member 2, said head portion 27 thereby further being configured with a ball element 30 fitting into the socket 14 of said socket portion 6 such that said first and second prosthesis members can at least pivot and rotate relative to each other.

It is thus also possible to allow the first and second prosthesis members 2, 4 to move relative to each other in the same ways as described above without dislocation or luxation of the prosthesis when said first and second prosthesis members are moved between positions corresponding to pronation and supination of a forearm of the human body.

The invention claimed is:

1. A prosthesis for reconstruction of a distal radioulnar joint after resection of a part of the ulna close to a distal end portion thereof,
    wherein the prosthesis (1) comprises a first prosthesis member (2), one or more fixation means (3) and a second prosthesis member (4),
    wherein the first prosthesis member (2) is configured for fixation to the distal end portion (U1) of the ulna,
    wherein the fixation means (3) is/are configured to extend into the radius (R) via said distal end portion (U1) of the ulna for immovably locking said distal end portion (U1) of the ulna to the radius (R),
    wherein the second prosthesis member (4) is configured for fixation to the ulna proximally of a space (US) which is defined between the distal end portion (U1) of the ulna and the ulna (U2) proximally of said space (US) by the resection of the part of the ulna close to said distal end portion (U1) of the ulna,
    wherein the second prosthesis member (4) is configured to extend into said space (US) for being joined with said first prosthesis member (2) in a manner which allows said first and second prosthesis members (2, 4) to at least pivot and rotate relative to each other,
    wherein the first prosthesis member (2) comprises a socket portion (6) which is configured with a socket (14) and a mounting portion (7) which is configured for fixation of said socket portion (6) in a cavity (CU) in the surface (U1c) of the distal end portion (U1) of the ulna facing the space (US) which is defined between the distal end portion (U1) of the ulna and the ulna (U2) proximally of said space (US),
    wherein the second prosthesis member (4) comprises a mounting portion (26) which is configured for fixation in the marrow cavity (MCU) of the ulna (U2) proximally of said space (US) between the distal end portion (U1) of the ulna and the ulna (U2) proximally of said space (US), and a head portion (27) which is configured to extend into said space (US) for joining said second prosthesis member (4) with said first prosthesis member (2), said head portion (27) thereby further being configured with a ball element (30) fitting into the socket (14) of said socket portion (6) such that said first and second prosthesis members (2, 4) can at least pivot and rotate relative to each other.

2. The prosthesis according to claim 1, wherein the mounting portion (7) of the first prosthesis member (2) is at least partly configured with an external thread for fixation by screwing said mounting portion (7) into the cavity (CU) in the surface (U1c) of the distal end portion (U1) of the ulna facing the space (US) which is defined between the distal end portion (U1) of the ulna and the ulna (U2) proximally of said space (US).

3. The prosthesis according to claim 2, wherein the mounting portion (7) of the first prosthesis member (2) is configured as a threaded part, and wherein the socket portion (6) of the first prosthesis member (2) has a mounting pin (9) which is insertable into a hole (10) in the (7) threaded part for attaching the socket portion (6) thereto.

4. The prosthesis according to claim 3, wherein the hole (10) in the threaded part and the mounting pin (9) of the socket portion (6) are configured with complementary portions for fastening of the socket portion (6) in the threaded part.

5. The prosthesis according to claim 4, wherein the hole (10) in the threaded part comprises, at the bottom, a snap-in attachment (17) for the mounting pin (9) of the socket portion (6) and
wherein the mounting pin (9) of the socket portion (6) is configured with snap-in portions (18) which engage the snap-in attachment (17) in the hole (10) in the threaded part.

6. The prosthesis according to claim 4, wherein the hole (10) in the threaded part and the mounting pin (9) of the socket portion (6) are configured such that said threaded part and said socket portion (6) define a press fit which permits bringing the socket portion (6) and the threaded part to attach to each other by pressing them together.

7. The prosthesis according to claim 6, wherein the hole (10) in the threaded part and the mounting pin (9) of the socket portion (6) are conically shaped.

8. The prosthesis according to claim 3, wherein the hole (10) in the threaded part and a part (20) defining the socket (14) of the socket portion (6) are configured with complementary portions which prevent rotation of the socket portion (6) relative to the threaded part, wherein the complementary parts are at least one recess (21) of the threaded part and at least one protrusion (22) of the socket (14).

9. The prosthesis according to claim 8, wherein the prosthesis comprises an opening (12) to the hole (10) in the threaded part, and wherein the hole (10) in the threaded part is configured with the at least one recess (21) on the inside of the opening (12) to said hole (10), and
wherein the socket portion (6) is configured with the at least one protrusion (22) externally on the part (20), the at least one protrusion (22) engaging the recess (21) in the hole (10) in the threaded part to prevent rotation of the socket portion (6) relative to the threaded part.

10. The prosthesis according to claim 3, wherein the socket portion (6), except for the mounting pin (9), comprises a part (20) defining the socket (14), said part being configured with a collar (23).

11. The prosthesis according to claim 3, wherein the prosthesis comprises an opening (12) to the hole (10) in the threaded part, and wherein the opening (12) to the hole (10) in the threaded part is provided with at least one recess (21) which is configured to permit insertion into said recess (21) of a driving portion (I2a) of a driving instrument (I2) for attachment by screwing of the threaded part to the distal end portion (U1) of the ulna.

12. The prosthesis according to claim 3, wherein the prosthesis comprises an opening (12) to the hole (10) in the threaded part, and wherein the bottom (13) of the hole (10) in the threaded part is configured as or with a groove to permit insertion into said groove of a driving portion (I2a) of a driving instrument (I2) for attachment by screwing of the threaded part to the distal end portion (U1) of the ulna.

13. The prosthesis according to claim 3, wherein the prosthesis comprises an opening (12) to the hole (10) in the threaded part, and wherein the threaded part of the first prosthesis member (2) is configured with a collar (16) around the opening (12) to the hole (10) for the socket portion (6) of said first prosthesis member (2), and
wherein the collar (16) is configured with an external thread.

14. The prosthesis according to claim 1, wherein the mounting portion (26) of the second prosthesis member (4) is at least partly configured with an external thread for fixation by screwing said mounting portion (26) into the marrow cavity (MCU) of the ulna (U2) proximally of the space (US) which is defined between the distal end portion (U1) of the ulna and the ulna (U2) proximally of said space (US).

15. The prosthesis according to claim 14, wherein the mounting portion (26) of the second prosthesis member (4) is configured as a threaded part, and
wherein the head portion (27) of the second prosthesis member (4) has a mounting pin (28) which is insertable into a hole (29) in the threaded part for attaching the head portion (27) thereto.

16. The prosthesis according to claim 15, wherein the hole (29) in the threaded part and the mounting pin (28) of the head portion (27) are configured with complementary portions for fastening of the head portion (27) in the threaded part.

17. The prosthesis according to claim 1, wherein the mounting portion (7) of the first prosthesis member (2) is at least partly configured with an external thread, the mounting portion (26) of the second prosthesis member (4) being at least partly configured with an external thread, and wherein the threads on the mounting portions (7, 26) of the first and second prosthesis members (2, 4) are self-tapping.

18. The prosthesis according to claim 1, wherein the first prosthesis member (2) is configured with one or more through-holes (25) for the fixation means (3).

19. The prosthesis according to claim 1, wherein the socket (14) of the socket portion (6) has such height that the first and second prosthesis members (2, 4) can move relative to each other substantially in the longitudinal direction of said first and second prosthesis members (2, 4) without dislocation or luxation of the prosthesis (1) when said first and second prosthesis members (2, 4) are moved between positions corresponding to pronation and supination of a forearm of the human body.

20. The prosthesis according to claim 1, wherein tension by means of which the ball element (30) of the head portion (27) is fitting into the socket (14) of the socket portion (6) is set such that the first and second prosthesis members (2, 4) can move relative to each other substantially in the longitudinal direction of said first and second prosthesis members (2, 4) without dislocation or luxation of the prosthesis (1) when said first and second prosthesis members (2, 4) are moved between positions corresponding to pronation and supination of a forearm of the human body.

21. Use of the prosthesis according to claim 1, for reconstruction of a proximal radioulnar joint after resection of a part of the radius (R) close to a proximal end portion (R1) thereof,
whereby the first prosthesis member (2) is configured for fixation to the proximal end portion (R1) of the radius,
whereby the fixation means (3) is/are configured to extend into the ulna (U) via said proximal end portion (R1) of the radius for immovably locking said proximal end portion (R1) of the radius (R) to the ulna (U),
whereby the second prosthesis member (4) is configured for fixation to the radius (R) distally of a space (RS) which is defined between the proximal end portion (R1) of the radius and the radius (R2) distally of said space (RS) by the resection of the part of the radius (R) close to said proximal end portion of the ulna (U), and whereby the second prosthesis member (4) is configured to extend into said space (RS) for being joined with said first prosthesis member (2) in a manner which allows said first and second prosthesis members (2, 4) to at least pivot and rotate relative to each other.

\* \* \* \* \*